(12) United States Patent
Jensen et al.

(10) Patent No.: US 9,636,086 B2
(45) Date of Patent: May 2, 2017

(54) THREE DIMENSIONAL (3D) TRANSVERSE OSCILLATION VECTOR VELOCITY ULTRASOUND IMAGING

(75) Inventors: Jorgen Arendt Jensen, Horsholm (DK); Michael Johannes Pihl, Kobenhavn N (DK)

(73) Assignee: B-K Medical Aps, Herlev (DK)

( * ) Notice: Subject to any disclaimer, the term of this patent is extended or adjusted under 35 U.S.C. 154(b) by 123 days.

(21) Appl. No.: 14/350,500

(22) PCT Filed: Oct. 11, 2011

(86) PCT No.: PCT/IB2011/002383
§ 371 (c)(1),
(2), (4) Date: Apr. 8, 2014

(87) PCT Pub. No.: WO2013/054149
PCT Pub. Date: Apr. 18, 2013

(65) Prior Publication Data
US 2014/0257103 A1    Sep. 11, 2014

(51) Int. Cl.
*A61B 8/08* (2006.01)
*G01P 5/24* (2006.01)
(Continued)

(52) U.S. Cl.
CPC .............. *A61B 8/5223* (2013.01); *A61B 8/06* (2013.01); *A61B 8/145* (2013.01); *A61B 8/4488* (2013.01);
(Continued)

(58) Field of Classification Search
None
See application file for complete search history.

(56) References Cited

U.S. PATENT DOCUMENTS

| 5,105,816 A | * | 4/1992 | Shimura | ................. A61B 8/06 600/454 |
| 5,910,119 A | | 6/1999 | Lin | |

(Continued)

OTHER PUBLICATIONS

International search report for PCT/IB2011/002383 published as WO 2013/054149.

(Continued)

*Primary Examiner* — Tse Chen
*Assistant Examiner* — Joanne Hoffman
(74) *Attorney, Agent, or Firm* — Anthony M. Del Zoppo, III; Driggs, Hogg, Daugherty & Del Zoppo, Co., LPA

(57) ABSTRACT

An ultrasound imaging system (300) includes a transducer array (302) with a two-dimensional array of transducer elements configured to transmit an ultrasound signal and receive echoes, transmit circuitry (304) configured to control the transducer array to transmit the ultrasound signal so as to traverse a field of view, and receive circuitry (306) configured to receive a two dimensional set of echoes produced in response to the ultrasound signal traversing structure in the field of view, wherein the structure includes flowing structure. A beamformer (312) configured to beamform the echoes, and a velocity processor (314) configured to separately determine a depth velocity component, a transverse velocity component and an elevation velocity component, wherein the velocity components are determined based on the same transmitted ultrasound signal and the same received set of two dimensional echoes.

25 Claims, 7 Drawing Sheets

(51) Int. Cl.
    G01S 15/89    (2006.01)
    A61B 8/06     (2006.01)
    A61B 8/14     (2006.01)
    A61B 8/00     (2006.01)

(52) U.S. Cl.
    CPC ............. A61B 8/463 (2013.01); G01P 5/244 (2013.01); G01S 15/8984 (2013.01); G01S 15/8993 (2013.01)

(56) References Cited

U.S. PATENT DOCUMENTS

| | | | | |
|---|---|---|---|---|
| 6,148,224 | A * | 11/2000 | Jensen | G01P 3/64 324/306 |
| 6,859,659 | B1 * | 2/2005 | Jensen | G01S 15/8984 342/108 |
| 2007/0208254 | A1 * | 9/2007 | Johnson | A61B 8/14 600/459 |

OTHER PUBLICATIONS

Jesper Udesen and Jorgen Arendt Jensen, Investigation of Transverse Oscillation Method, IEEE Transactions on Ultrasonics, Ferroelectrics and Frequency Control, vol. 53, No. 5, May 2006.

Jesper Udesen, et al., Examples of In Vivo Blood Vector Velocity Estimation, Ultrasound in Med. & Biol., vol. 33, No. 4, pp. 541-548, 2007.

Peter Munk and Jorgen Arendt Jensen, Performance of Velocity Vector Estimation Using an Improved Dynamic Beamforming Setup, Invited paper presented at the SPIE Medical Imaging meeting, Ultrasonic Imaging and signal processing, 2001: Proceedings of SPIE, vol. 4325, pp. 227-241, Eds. M.F. Insana and K.K. Shung, 2001; Center for fast Ultrasound Imaging, DK.

Peter Munk and Jorgen Arendt Jensen, Performance of a vector velocity estimator, IEEE Ult. symp., 1998, P. Munk and J.A. Jensen, Paper presented at the IEEE International Ultrasonics Symposium, Sendai, Japan, 1998: To be published in Proceedings of IEEE International Ultrasonics Symposium, Sendai, Japan, 1998.

Mads Moller Pedersen, et al., Preliminary Comparison between real-time in vivo Spectral and Transverse Oscillation velocity estimates.

Jorgen Arendt Jensen, A New Estimator for Vector Velocity Estimation, IEEE Transactions on Ultrasonics, Ferroelectrics and Frequency Control, vol. 48, No. 4, Jul. 2001.

Jorgen Arendt Jensen and Peter Munk, A New Method for Estimation of Velocity Vectors, IEEE Transactions of Ultrasonics, Ferroelectrics, and Frequency Control, vol. 45, No. 3, May 1998.

Jorgen Arendt Jensen, et al., Vector blood velocity estimation in medical ultrasound, 5th International Symposium on Ultrasonic Doppler Methods for Fluid Mechanics and Fluid Engineering.

* cited by examiner

THREE DIMENSIONAL (3D) TRANSVERSE OSCILLATION VECTOR VELOCITY ULTRASOUND IMAGING

RELATED APPLICATION

This application is a national filing of PCT application Ser. No. PCT/IB2011/002383, filed Oct. 11, 2011, published as WO/2013/054149 on Apr. 18, 2013.

TECHNICAL FIELD

The following generally relates to ultrasound imaging and more particularly to three dimensional (3D) transverse oscillation vector velocity ultrasound imaging which can be used to estimate the spatial velocity components (depth, transverse and elevation) of blood flow velocity and/or moving tissue structures.

BACKGROUND

Ultrasound imaging provides useful information about the interior characteristics of an object or subject such as a human or animal patient. In one instance, an ultrasound scanner has been used to estimate blood flow velocity and generate one or more images of the interior characteristics with the estimated blood velocity superimposed there over.

With conventional ultrasound imaging blood flow velocity estimation, a pulse-echo field only oscillates in the axial direction along the axis of the ultrasound beam. This is illustrated in FIG. 1 in which an ultrasound beam 102 propagates along a z-axis 104 and only the axial velocity component (vz) 106 along the z-axis or depth can be estimated; the transverse velocity components vx 108 and vy 110 cannot be estimated. Blood scatterers passing through the field of interest will produce a signal with a frequency component proportional to the axial velocity. The basic mechanism that allows the traditional estimation of axial velocities is the oscillations in the transmitted pulse.

The transverse oscillation (TO) blood velocity estimation approach has been used to estimate vz and vx. Using the same basic mechanism noted above, a transverse oscillation is introduced in the ultrasound field, and this oscillation generates received signals that depend on the transverse oscillation. The basic idea is to create a double-oscillating pulse-echo field using a one dimensional (1D) transducer array. This had been accomplished by using the same transmit beam as used in conventional velocity estimation and particularly predetermined apodization profiles in receive. Suitable apodization functions are discussed in J. A. Jensen and P. Munk, "A New Method for Estimation of Velocity Vectors," IEEE Trans. Ultrason., Ferroelec., Freq. Contr., vol. 45, pp. 837-851, 1998, and J. Udesen and J. A. Jensen, "Investigation of Transverse Oscillation Method," IEEE Trans. Ultrason., Ferroelec., Freq. Contr., vol. 53, pp. 959-971, 2006.

FIG. 2 shows an example of the TO approach for estimating vz and vx. In this example, the transverse oscillations are created in receive, and two lines are beamformed in parallel to get the spatial lateral in-phase (I) and quadrature (Q) components. The spatial IQ samples, $r_{IQ}$, are obtained by $r_{IQ}(t)=r_I(t)+jr_Q(t)$, where $r_I$ and $r_Q$ are the samples at time t from the left and right beam, respectively. Along with the two TO lines, a center line can be beamformed for conventional axial or depth velocity estimation. Using the Fraunhofer approximation, the relation between the lateral spatial wavelength and the apodization function is: $\lambda_x = 2\lambda_z z_0/d$, where d is the distance between the two peaks in the apodization function, $z_0$ is depth, and $\lambda_z$ is the axial wavelength.

From the above apodization function, the lateral wavelength ($\lambda_x$) increases as the depth ($z_0$) increases, if the apodization function (d) is kept constant. To keep a constant lateral wavelength ($\lambda_x$), the aperture must expand with depth ($z_0$). Using a phased array, the width is often limited, so instead the spacing between the two beamformed lines can be increased through depth. Keeping the apodization function fixed, the two lines can be beamformed with a fixed angle. Using the tangent-relation, the angle, θ, between the two lines can be derived as $\theta/2 = \arctan((\lambda_x/8)/z_0) = \arctan(\lambda_z/4d)$.

If $r_{IQ}$ is the spatial IQ signal, then the corresponding temporal IQ signal can be referred to as $r_{IQ,h}$, and two new signals, $r_1$ and $r_2$, can be generated $r_1(k)=r_{IQ}(k)+jr_{IQ,h}(k)$ and $r_2(k)=r_{IQ}(k)-jr_{IQ,h}(k)$, where k denotes discrete samples. The transverse velocity (vx) can then be calculated by:

$$vx = \left(\frac{\lambda_x}{2\pi 2kT_{prf}}\right)\arctan\left(\frac{\Im\{R_1(k)\}\Re\{R_2(k)\}+\Im\{R_2(k)\}\Re\{R_1(k)\}}{\Re\{R_1(k)\}\Re\{R_2(k)\}-\Im\{R_2(k)\}\Im\{R_1(k)\}}\right),$$

where $T_{prf}$ is the time between two pulses, $R_1(k)$ is the complex lag k autocorrelation value for $r_1(k)$, and $R_2(k)$ is the complex lag k autocorrelation value for $r_2(k)$. The complex autocorrelation is estimated over N shots, and is typically spatially averaged over a pulse length.

Three dimensional (3D) velocity approaches for estimating vz, vx and vy are discussed in M. D. Fox, "Multiple crossed-beam ultrasound Doppler velocimetry," IEEE Trans. Son. Ultrason., vol. SU-25, pp. 281-286, 1978, and G. E. Trahey, J. W. Allison, and O. T. von Ramm, "Angle independent ultrasonic detection of blood flow," IEEE Trans. Biomed. Eng., vol. BME-34, pp. 965-967, 1987. Unfortunately, Fox uses a multi-beam approach that requires trigonometry to determine velocity, and Trahey uses speckle tracking (normalized cross-correlation) to determine a three dimensional (3D) velocity vector from the entire acquired 3D volume of data.

SUMMARY

Aspects of the application address the above matters, and others.

In one aspect, an ultrasound imaging system includes a transducer array with a two-dimensional array of transducer elements configured to transmit an ultrasound signal and receive echoes, transmit circuitry configured to control the transducer array to transmit the ultrasound signal so as to traverse a field of view, and receive circuitry configured to receive a two dimensional set of echoes produced in response to the ultrasound signal traversing structure in the field of view, wherein the structure includes flowing structure. A beamformer configured to beamform the echoes, and a velocity processor configured to separately determine a depth velocity component, a transverse velocity component and an elevation velocity component, wherein the velocity components are determined based on the same transmitted ultrasound signal and the same received set of two dimensional echoes.

In another aspect, a method includes receiving a two dimensional set of echoes corresponding to a same transmit ultrasound signal. The method further includes concurrently generating a line of data along a z direction in which the transmitted ultrasound signal traverses, a pair of lines of data in a z-x plane, and a pair of lines of data in a z-y plane, which is perpendicular to the z-x plane based on the received two dimensional set of echoes. The method further includes estimating a depth velocity component based on the line of data, a transverse velocity component based on the pair of lines of data in a z-x plane, and an elevation velocity component pair of lines of data in a z-y plane.

In another aspect, a velocity processor includes a depth velocity processor, a transverse velocity processor, and an elevation velocity processor. The depth, transverse velocity and elevation velocity processors respectively generates signals indicative of a depth velocity component in a z direction along which a transmit ultrasound signal traverses, a transverse velocity component traversing a z-x plane, and an elevation velocity component traversing a z-y plane, based on a two dimensional set of echoes received in response to the same transmit ultrasound signal.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which.

DETAILED DESCRIPTION

Figure 1:
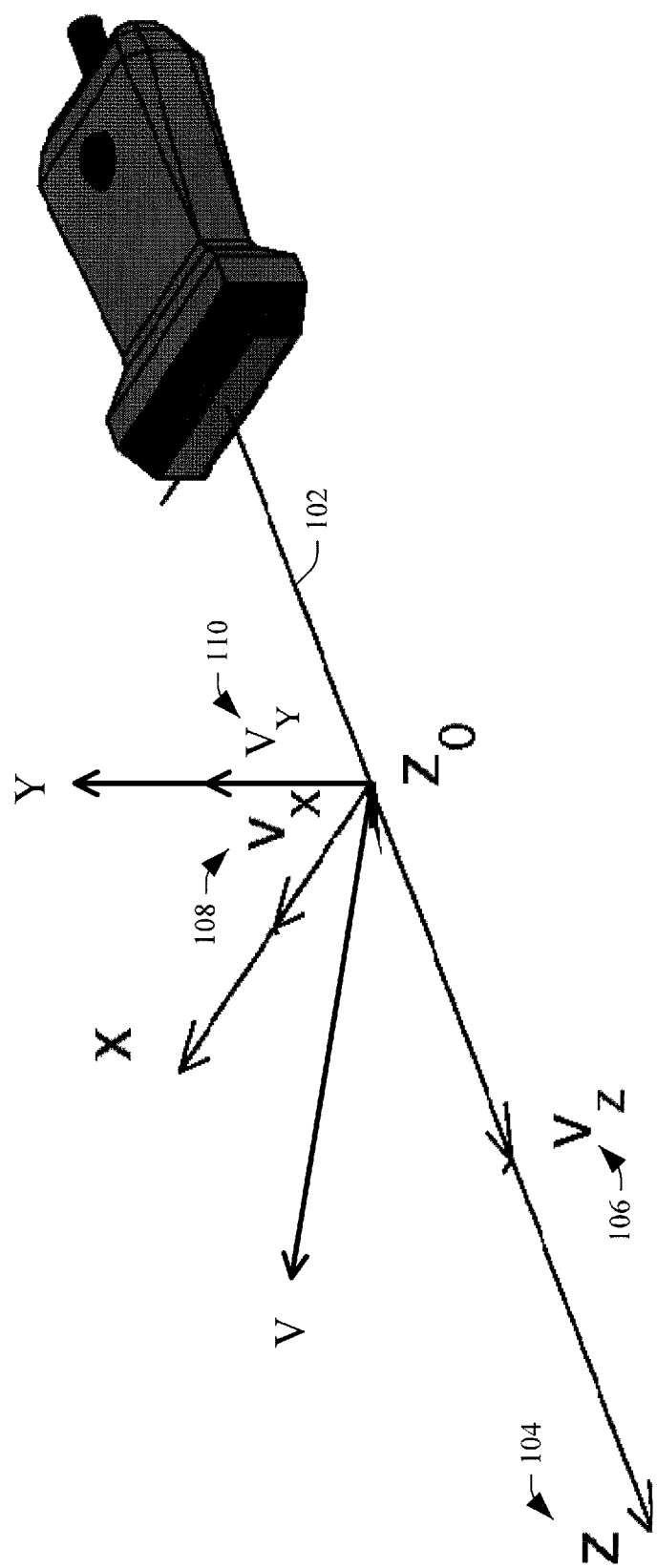
FIG. 1 illustrates a prior art approach to estimating flow and/or tissue velocity along the depth of the transmitted ultrasound signal.
Figure 2:
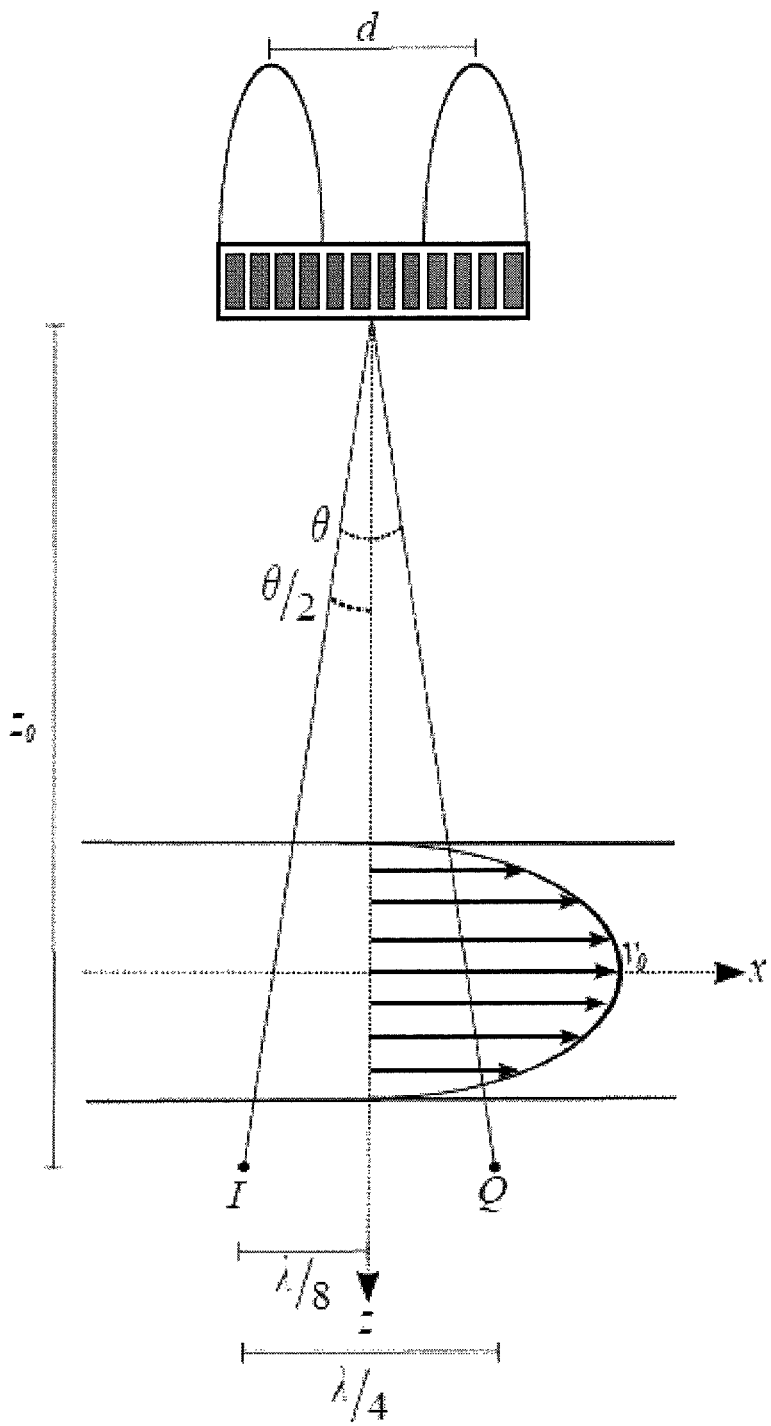
FIG. 2 illustrates a prior art approach to estimating flow and/or tissue velocity along the depth of the transmitted ultrasound signal and along a transverse direction.
Figure 3:
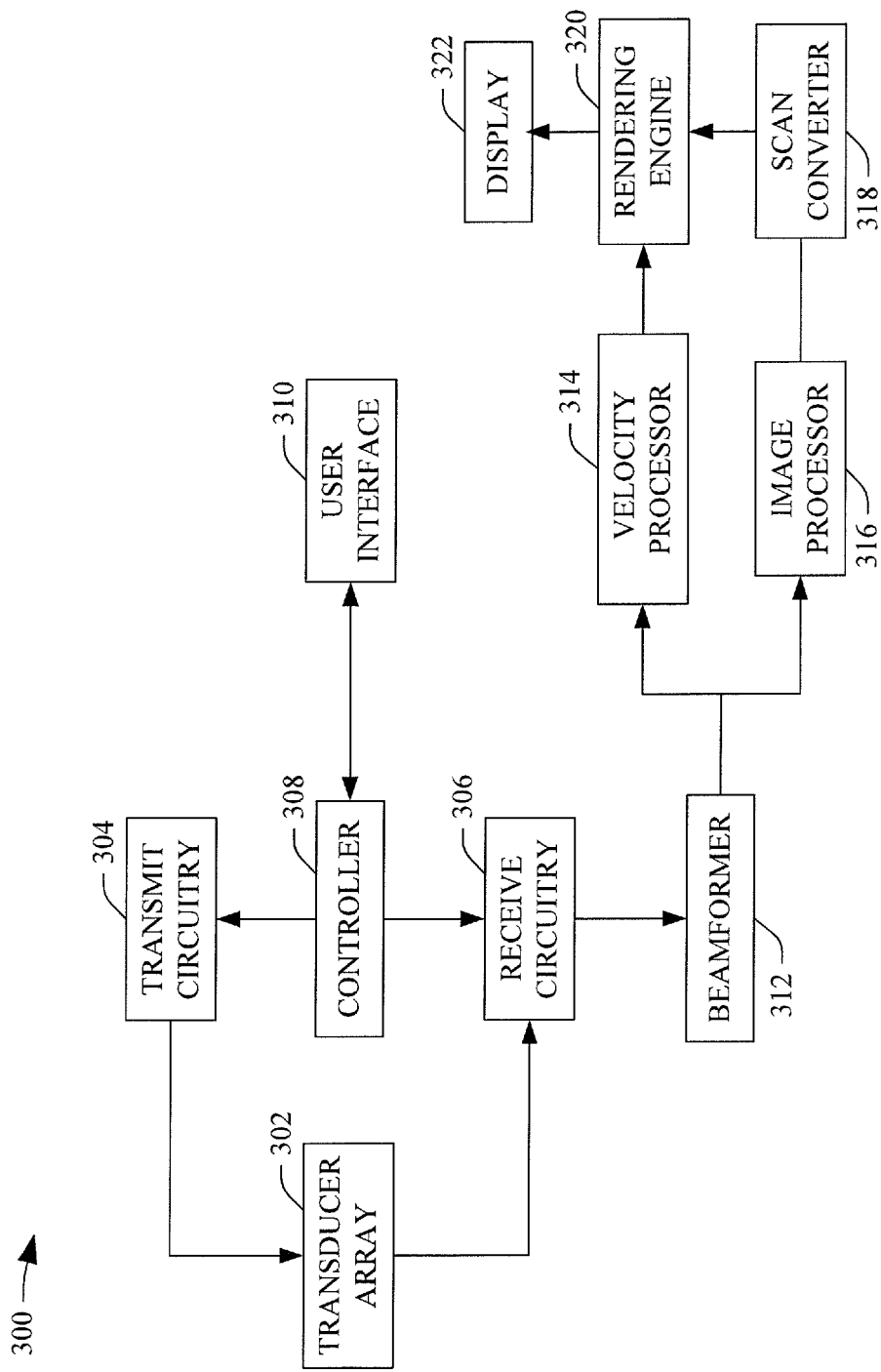
FIG. 3 schematically illustrates an example ultrasound imaging system in connection with a beamformer and velocity processor for determining velocity in depth, transverse and elevation directions.

Initially referring to FIG. 3, an example ultrasound imaging system 300 is illustrated.

A transducer array 302 includes a two dimensional (2D) array of transducer elements, which are configured to transmit ultrasound signals and receive echo signals. Examples of suitable 2D arrays include 32×32, 64×64, and/or other dimension arrays, including square and/or rectangular arrays. The array can be linear, curved, and/or otherwise shaped. The array can be fully populated or sparse and/or a combination hereof.

Transmit circuitry 304 generates a set of pulses that are conveyed to the transducer array 302. The set of pulses actuates a corresponding set of the transducer elements of the transducer array 304, causing the elements to transmit ultrasound signals into an examination or scan field of view. In the illustrated embodiment, transmit circuitry 304 generates a set of pulses which produce a transmit signal suitable at least for velocity imaging.

Receive circuitry 306 receives echoes generated in response to the transmitted ultrasound signals from the transducer 302. The echoes, generally, are a result of the interaction between the emitted ultrasound signals and the structure (e.g., flowing blood cells, organ cells, etc.) in the scan field of view.

A controller 308 controls one or more of the transmit circuitry 304 or receive circuitry 306. Such control can be based on available modes of operation (e.g., velocity flow, A-mode, B-mode, etc.) of the system 300. In addition, such control can be based on one or more signals indicative of input from a user via a user interface (UI) 310. The UI 310 may include one or more input devices (e.g., a button, a knob, a slider, a touch pad, etc.) and/or one or more output devices (e.g., a display screen, lights, a speaker, etc.).

A beamformer 312 processes the echoes, for example, by applying time delays, weighting on the channels, summing, and/or otherwise beamforming received echoes. As described in greater detail below, in one instance, the beamformer 312 includes a plurality of beamformers that simultaneously process the echoes and produce data for determining the three dimensional (3D) velocity components, vz (depth velocity), vx (transverse velocity) and vy (elevation velocity). The illustrated beamformer 312 also produces data for generating images in A-mode, B-mode, and/or other modes.

A velocity processor 314 processes the beamformed data output by the beamformer 312 output. This includes processing the beamformed data to determine one or more of the 3D velocity components, vz, vx or vy. As described in greater detail below, in one instance the velocity processor 314 individually and separately estimates vz, vx or vy based on a same transmission ultrasound signal and the corresponding two dimensional (2D) acquired data.

An image processor 316 also receives the beamformed data from the beamformer 312. For B-mode, the image processor 316 processes the data and generates a sequence of focused, coherent echo samples along focused scanlines of a scanplane. The image processor 316 may also be configured to process the scanlines to lower speckle and/or improve specular reflector delineation via spatial compounding and/or perform other processing such as FIR filtering, IIR filtering, etc.

A scan converter 318 scan converts the output of the image processor 316 to generate data for display, for example, by converting the data to the coordinate system of the display. The scan converter 318 can be configured to employ analog and/or digital scan converting techniques.

A rendering engine 320 visually presents one or more images and/or velocity information via a display monitor 322. Such presentation can be in an interactive graphical user interface (GUI), which allows the user to selectively rotate, scale, and/or manipulate the displayed data. Such interaction can be through a mouse or the like, and/or a keyboard or the like, touch-screen controls and/or the like, and/or other known and/or approach for interacting with the GUI.

It is to be appreciated that the beamformer 312 and/or the velocity processor 314 can be implemented via a processor executing one or more computer readable instructions encoded or embedded on computer readable storage medium such as physical memory. Such a processor can be part of the system 300 and/or a computing device remote from the system 300. Additionally or alternatively, the processor can execute at least one computer readable instructions carried by a carrier wave, a signal, or other non-computer readable storage medium such as a transitory medium.

Figure 4:
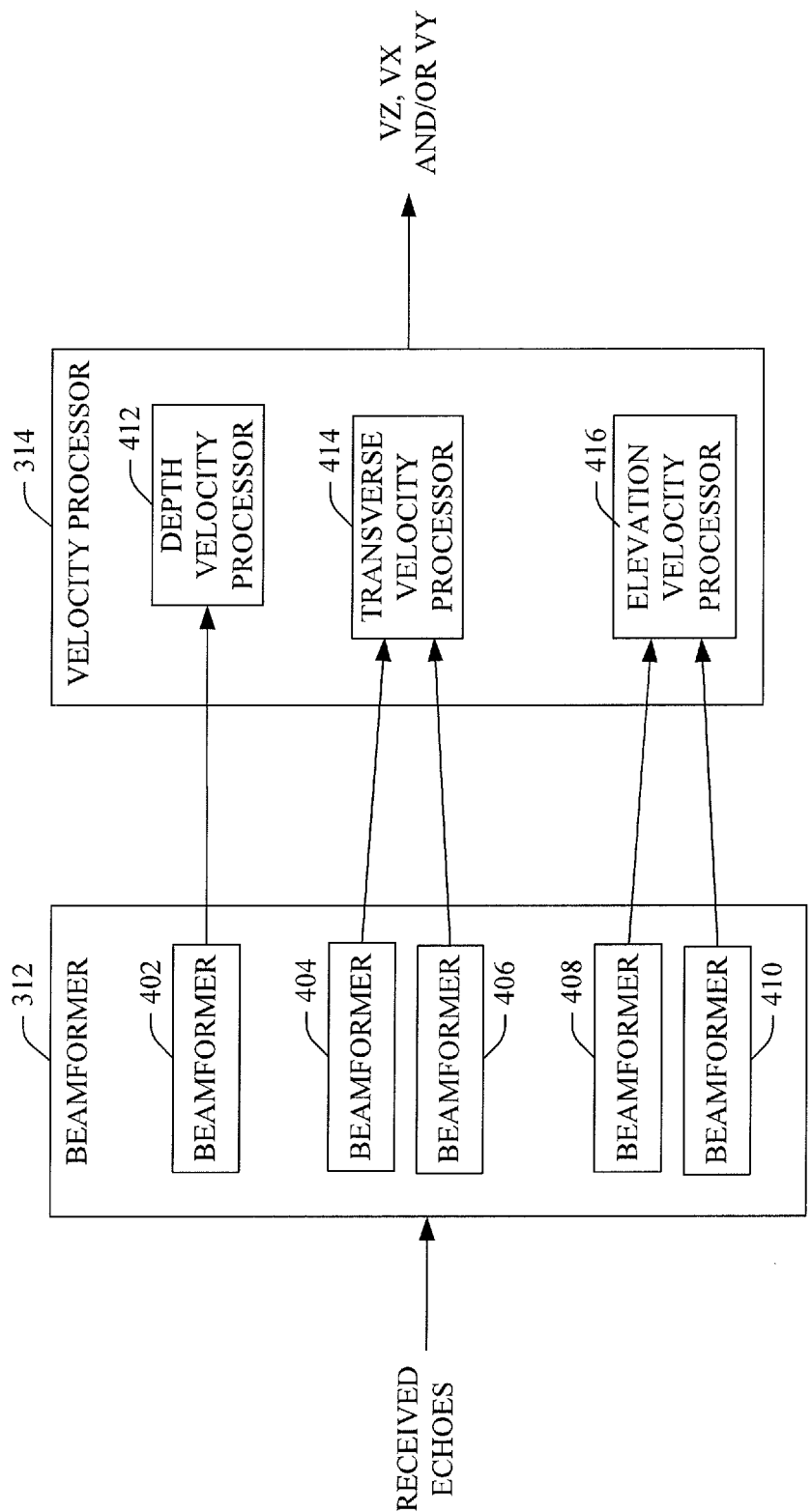
FIG. 4 schematically illustrates examples of the beamformer and velocity processor of FIG. 3.
Figure 5:
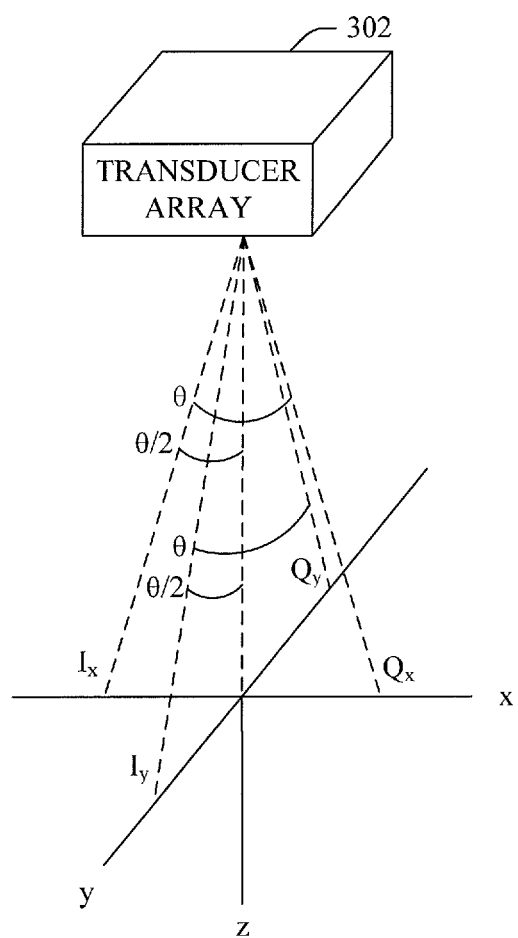
FIG. 5 illustrates beamformed lines for producing data for determining velocity in depth, transverse and elevation directions.

FIGS. 4 and 5 illustrate a non-limiting example. FIG. 4 depicts examples of the beamformer 312 and the velocity processor 314, and FIG. 5 depicts the beamformed data used to determine the velocities vz, vx and/or vy. For this example, the transmit circuitry 304 (FIG. 3) controls the transducer array 302 (FIG. 3) so that a lateral width of the transmitted pulse is broad enough to cover the beamformed receive lines. This can be done using a high F-number, a focal depth further away than the depth of interest, plane waves, or other approach. The transverse oscillations are created in receive.

The beamformer 312 includes five (5) beamformers 402, 404, 406, 408 and 410. The beamformer 402 is configured to produce data for determining vz, the beamformers 404 and 406 are configured to produce data for determining vx, and beamformers 408 and 410 are configured to produce data for determining vy. The beamformers 404 and 406 have apodization peaks that are separated or spaced apart by a predetermined distance and simultaneously create the lines Ix and Qx in the z-x plane. The beamformers 408 and 410 have apodization peaks that are separated or spaced apart by a predetermined distance and simultaneously create the lines Iy and Qy in the z-y plane. The apodization of vx and vy is ninety degrees (90°) apart.

In this example, the lines Ix, Qx, Iy and Qy are beamformed based on a same fixed angle θ that corresponds to an increasing lateral wavelength. In another embodiment, the lines Ix and Qx and the lines Iy and Qy can be beamformed based on different fixed angles or a fixed distance between them. In this example, all five of the lines z, Ix, Qx, Iy and Qy are beamformed simultaneously. In another embodiment, all five of the lines z, Ix, Qx, Iy and Qy are not beamformed simultaneously. In yet another embodiment, the beamformer 312 includes more than five beamformers in which several velocity image lines are beamformed in parallel.

The velocity processor 314 includes a depth processor 412 that processes the data generated by the beamformer 402 and estimates vz, a transverse processor 414 that processes the data generated by the beamformers 404 and 406 and estimates vx, and an elevation processor 416 that processes the data generated by the beamformers 408 and 410 and estimates vy. The depth processor 412 can use a conventional autocorrelation and/or other approach to estimate vz. The transverse processor 414 and the elevation processor 416 can use a transverse oscillation (TO) approach to determine vx and vy.

For example, from above, for vx, the Fraunhofer approximation can be used to determine the $\lambda_x = 2\lambda_z z_0/d$, where d is the distance between the two peaks in the apodization function, $z_0$ is depth, and $\lambda_z$ is the axial wavelength. Alternatively, $\lambda_x$ can be determined based on the simulated or measured pulse-echo field. The Fraunhofer approximation can similarly be used for vy in which the relation is $\lambda_y = 2\lambda_z z_0/d$. Using the tangent-relation, the angle between the two lines is $\theta/2 = \arctan((\lambda_y/8)/z_0) = \arctan(\lambda_y/4d)$. Using the same constraints as used for vx, the elevation velocity (vy) can then be calculated by:

$$vy = \left(\frac{\lambda_y}{2\pi 2k T_{prf}}\right) \arctan\left(\frac{\Im\{R_1(k)\}\Re\{R_2(k)\} + \Im\{R_2(k)\}\Re\{R_1(k)\}}{\Re\{R_1(k)\}\Re\{R_2(k)\} - \Im\{R_2(k)\}\Im\{R_1(k)\}}\right),$$

where $T_{prf}$ is the time between two pulses, $R_1(k)$ is the complex lag k autocorrelation value for $r_1(k)$, and $R_2(k)$ is the complex lag k value for $r_2(k)$. From above, $$vx = \left(\frac{\lambda_x}{2\pi 2k T_{prf}}\right) \arctan\left(\frac{\Im\{R_1(k)\}\Re\{R_2(k)\} + \Im\{R_2(k)\}\Re\{R_1(k)\}}{\Re\{R_1(k)\}\Re\{R_2(k)\} - \Im\{R_2(k)\}\Im\{R_1(k)\}}\right).$$

Figure 6:
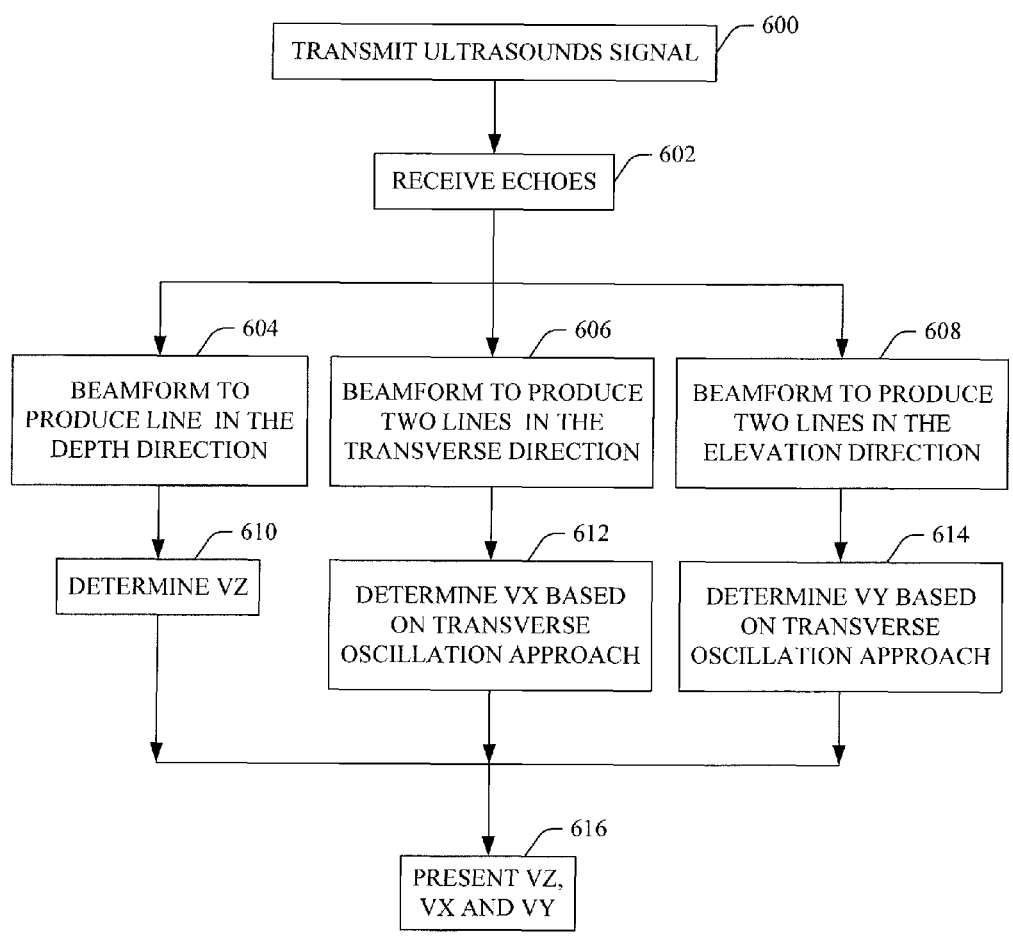
FIG. 6 illustrates a method.

FIG. 6 illustrates an example method for employing the ultrasound imaging system.

It is to be understood that the following acts are provided for explanatory purposes and are not limiting. As such, one or more of the acts may be omitted, one or more acts may be added, one or more acts may occur in a different order (including simultaneously with another act), etc.

At 600, an ultrasound signal is transmitted into a field of view.

At 602, echoes, in response to the ultrasound signal, are received by a two dimensional transducer array.

At 604, the echoes are beamformed to produce a line along the depth direction z.

At 606, the echoes are beamformed to produce two lines, separated by a fixed angle, in the z-x plane.

At 608, the echoes are beamformed to produce two lines, separated by a fixed angle, in the z-y plane.

In this embodiment, acts 604-608 are performed concurrently and independently. However, it is to be appreciated that acts 604-608 do not have to be performed concurrently and independently.

At 610, vz is determined based on the line in the depth direction z, for example, using autocorrelation.

At 612, vx is determined based on the two lines in the z-x plane using the transverse oscillation approach.

At 614, vz is determined based on the two lines in the z-y plane using the transverse oscillation approach.

At 616, the velocities vz, vx and vy are visually presented. In one instance, this includes superimposing the data corresponding to the velocities vz, vx and vy over a B-mode or other image.

The methods described herein may be implemented via one or more processors executing one or more computer readable instructions encoded or embodied on computer readable storage medium such as physical memory which causes the one or more processors to carry out the various acts and/or other functions and/or acts. Additionally or alternatively, the one or more processors can execute instructions carried by transitory medium such as a signal or carrier wave.

Figure 7:
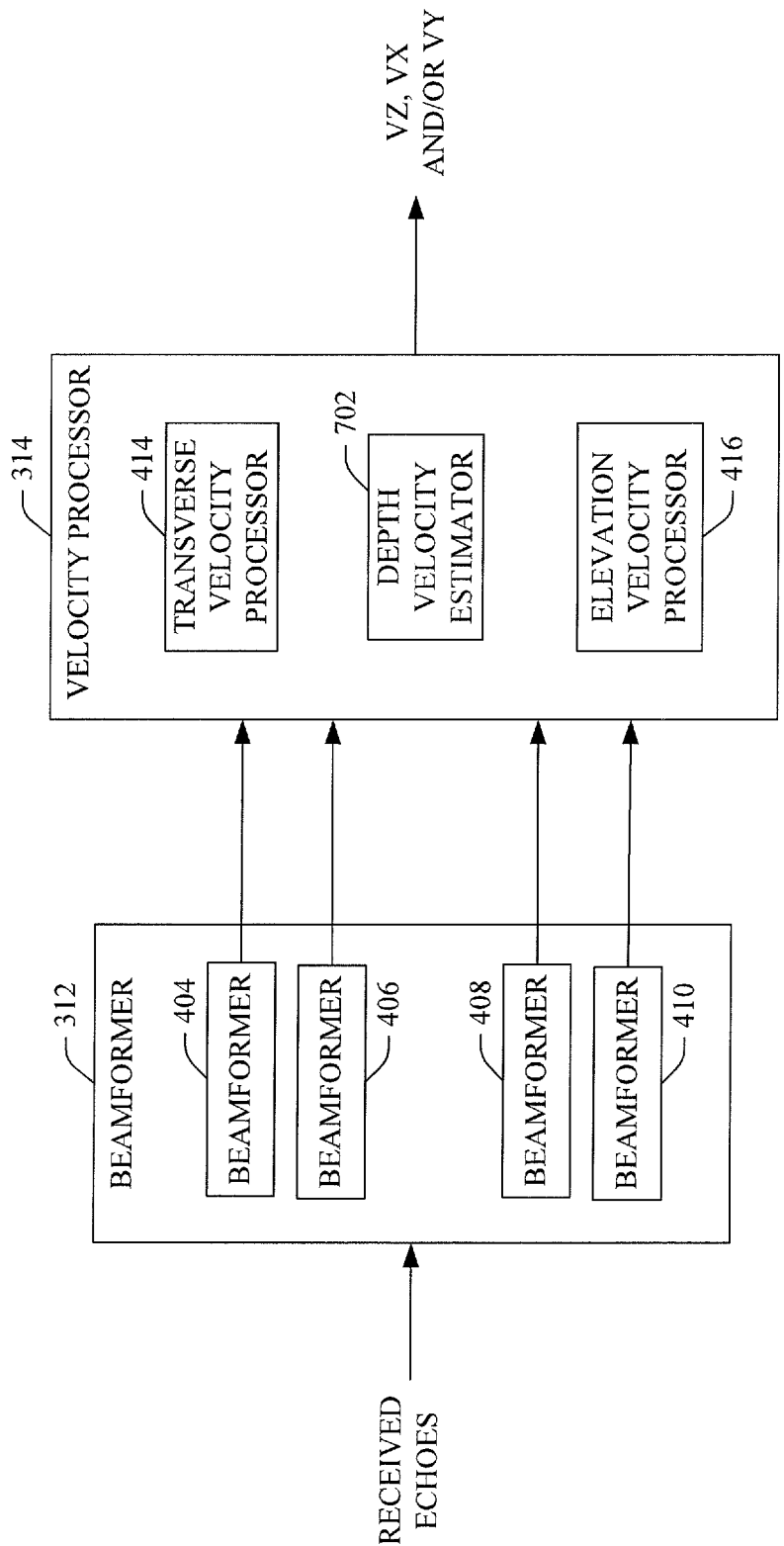
FIG. 7 schematically illustrates a variation of the embodiment of FIG. 4.

FIG. 7 schematically illustrates a variation of the embodiment of FIG. 4. In this variation, only four (4) lines are beamformed instead of five (5). More specifically, the beamformers 404 and 406 beamform respective lines, which the transverse velocity processor 414 processes, using a TO approach, to estimate vx, and the beamformers 408 and 410 beamform respective lines, which the elevation velocity processor 416 processes, using a TO approach, to estimate vy. In this variation, the velocity processor 314 includes a depth velocity estimator 702, which estimates vz based on the two lines used to determine vx and/or the two lines used to determine vy. The beamformer 402 and/or the depth velocity processor 412 can be omitted. In another variation, the depth velocity processor 412 and the depth velocity estimator 702 are part of the same depth velocity component.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound imaging system, comprising:
   a transducer array, including a two-dimensional array of transducer elements configured to transmit an ultrasound signal and receive echoes;
   transmit circuitry configured to control the transducer array to transmit the ultrasound signal so as to traverse a field of view;
   receive circuitry configured to receive a two dimensional set of echoes produced in response to the ultrasound signal traversing structure in the field of view, wherein the structure includes flowing structure;
   a beamformer with only four sub-beamformers, which concurrently beamform scanlines, and each of the sub-beamformers beamforms one scanline for a total of four scanlines, wherein the beamformer is configured to beamform the echoes, producing at least a pair of I/Q lines in a depth/elevation plane and separated by a first angle and a pair of I/Q lines in a depth/transverse plane and separated by a second angle for a total of two pairs of I/Q lines, wherein each line of the two pairs of I/Q lines is one of the four scanlines; and
   a processor configured to separately determine a depth velocity component, a transverse velocity component and an elevation velocity component independent of each other, wherein the processor determines the depth, transverse and elevation velocity components from a same transmitted ultrasound signal and a same received set of two dimensional echoes, and determines the elevation velocity component from the pair of I/Q lines in a depth/elevation plane, the transverse velocity component from the pair of I/Q lines in a depth/transverse plane, and the depth velocity component from at least one of the pairs of I/Q lines in the depth/elevation plane or the depth/transverse plane,
   wherein the processor determines the elevation velocity component from:

$$\left(\frac{\lambda_y}{2\pi 2kT_{prf}}\right)\arctan\left(\frac{\Im\{R_1(k)\}\Re\{R_2(k)\} + \Im\{R_2(k)\}\Re\{R_1(k)\}}{\Re\{R_1(k)\}\Re\{R_2(k)\} - \Im\{R_2(k)\}\Im\{R_1(k)\}}\right),$$

where $\lambda_y$ is an elevation wavelength, $T_{prf}$ is a time between two ultrasound pulses, k is a lag, and $R_1(k)$ and $R_2(k)$ are complex lag k autocorrelation values.

2. The system of claim 1, wherein the beamformer concurrently beamforms the echoes.

3. The system of claim 1, wherein the processor determines the transverse velocity component based on a transverse oscillation.

4. The system of claim 1, wherein the processor determines the elevation velocity component based on a transverse oscillation.

5. The system of claim 1, wherein pairs of two lines beamformed by the beamformer include lines that are separated by a fixed receive angle.

6. The system of claim 1, wherein sets of two lines beamformed by the beamformer are separated by a quarter wavelength.

7. The system of claim 5, wherein the angle corresponds to an increasing lateral wavelength.

8. The system of claim 2, wherein the beamformer beamforms a line of data along a depth direction of the transmitted ultrasound signal, and the processor determines the depth velocity component based on the line.

9. The system of claim 1, wherein the processor determines the depth velocity component based on autocorrelation.

10. The system of claim 1, wherein the depth velocity component, the transverse velocity component and the elevation velocity component are perpendicular to each other.

11. The system of claim 1, wherein the depth velocity component represents velocity along a direction of the transmitted ultrasounds signal, the transverse velocity component represents velocity along a direction perpendicular to the direction of the depth velocity component, and the elevation velocity component represents velocity along a direction perpendicular to both the direction of the depth velocity component and the direction of the transverse velocity component.

12. A method, comprising:
    receiving, with transducer elements of a transducer array, a two dimensional set of echoes corresponding to a same transmit ultrasound signal and generating electrical signals indicative thereof;
    concurrently generating pair of lines of data in a z-x plane, and a pair of lines of data in a z-y plane, which is perpendicular to the z-x plane, based on the electrical signals; and
    estimating, independent of each other, a depth velocity component based on one of the pair of lines of data in a z-x plane or the pair of lines of data in a z-y plane, a transverse velocity component based on the pair of lines of data in a z-x plane, and an elevation velocity component based on the pair of lines of data in a z-y plane, wherein the elevation velocity component is estimated using:

$$\left(\frac{\lambda_y}{2\pi 2kT_{prf}}\right)\arctan\left(\frac{\Im\{R_1(k)\}\Re\{R_2(k)\} + \Im\{R_2(k)\}\Re\{R_1(k)\}}{\Re\{R_1(k)\}\Re\{R_2(k)\} - \Im\{R_2(k)\}\Im\{R_1(k)\}}\right),$$

where $\lambda_y$ is an elevation wavelength, $T_{prf}$ is a time between two ultrasound pulses, k is a lag, and $R_1(k)$ and $R_2(k)$ are complex lag k autocorrelation values.

13. The method of claim 12, further comprising:
    estimating the three velocity components individually and separately from each other.

14. The method of claim 12, further comprising:
    estimating the depth velocity component based on autocorrelation.

15. The method of claim 12, further comprising:
    estimating the transverse velocity component based on a transverse oscillation.

16. The method of claim 12, further comprising:
    estimating the elevation velocity component based on a transverse oscillation.

17. The method of claim 12, wherein the depth velocity component, the transverse velocity component and the elevation velocity component are perpendicular to each other.

18. The method of claim 12, wherein the depth velocity component represents velocity along a direction of the transmitted ultrasounds signal, the transverse velocity component represents velocity along a direction perpendicular to the direction of the depth velocity component, and the elevation velocity component represents velocity along a direction perpendicular to both the direction of the depth velocity component and the direction of the transverse velocity component.

19. An apparatus, comprising:
a beamformer configured to beamform only four scanlines, wherein the beamformer comprises: a first pair of beamformers configured to beamform a first pair of lines in a z-x plane; and a second different pair of beamformers to beamform a second pair of lines in a z-y plane; and
a processor configured to process the first pair of lines to estimate a transverse velocity component traversing the z-x plane, process the second pair of lines to estimate an elevation velocity component traversing the z-y plane, and process at least one of the first pair of lines and the second pair of lines to estimate a depth velocity in a z direction along which a transmit ultrasound signal traverses based on a two dimensional set of echoes received in response to the same transmit ultrasound signal, wherein the processor determines the elevation velocity component from:

$$\left(\frac{\lambda_y}{2\pi 2k T_{prf}}\right)\arctan\left(\frac{\Im\{R_1(k)\}\Re\{R_2(k)\} + \Im\{R_2(k)\}\Re\{R_1(k)\}}{\Re\{R_1(k)\}\Re\{R_2(k)\} - \Im\{R_2(k)\}\Im\{R_1(k)\}}\right),$$

where $\lambda_y$ is an elevation wavelength, $T_{prf}$ is a time between two ultrasound pulses, k is a lag, and $R_1(k)$ and $R_2(k)$ are complex lag k autocorrelation values.

20. The apparatus of claim 19, wherein the processor respectively generates the transverse velocity component and the elevation velocity component based on a transverse oscillation algorithm.

21. The ultrasound imaging system of claim 1, wherein the processor determines the transverse velocity component from:

$$\left(\frac{\lambda_y}{2\pi 2k T_{prf}}\right)\arctan\left(\frac{\Im\{R_1(k)\}\Re\{R_2(k)\} + \Im\{R_2(k)\}\Re\{R_1(k)\}}{\Re\{R_1(k)\}\Re\{R_2(k)\} - \Im\{R_2(k)\}\Im\{R_1(k)\}}\right),$$

where $\lambda_x$ is a transverse wavelength, $T_{prf}$ is a time between two ultrasound pulses, k is a lag, and $R_1(k)$ and $R_2(k)$ are complex lag k autocorrelation values.

22. The method of claim 12, further comprising:
processing beamformed echoes to generate a B-mode image;
visually presenting the B-mode image; and
visually presenting graphical indicia representing the depth, transverse and elevation velocity components superimposed over the B-mode image.

23. The apparatus of claim 19, wherein processor estimates the transverse velocity component and the depth velocity component independent of each other.

24. The apparatus of claim 19, wherein processor estimates the elevation velocity component and the depth velocity component independent of each other.

25. The method of claim 12, further comprising:
employing only four sub-beamformers, which concurrently beamform scanlines, to beamform only four lines of data, which include the pair of lines of data in the z-x plane and the pair of lines of data in the z-y plane, including:
beamforming, with a first of the four sub-beamformers, a first of the pair of lines of data in the z-x plane;
beamforming, with a second of the four sub-beamformers, a second of the pair of lines of data in the z-x plane;
beamforming, with a third of the four sub-beamformers, a first of the pair of lines of data in the z-y plane; and
beamforming, with a fourth of the four sub-beamformers, a second of the pair of lines of data in the z-y plane.

* * * * *